US005888519A

United States Patent [19]
Alving

[11] Patent Number: 5,888,519
[45] Date of Patent: Mar. 30, 1999

[54] ENCAPSULATED HIGH-CONCENTRATION LIPID A COMPOSITIONS AS IMMUNOGENIC AGENTS TO PRODUCE HUMAN ANTIBODIES TO PREVENT OR TREAT GRAM-NEGATIVE BACTERIAL INFECTIONS

[75] Inventor: Carl R. Alving, Bethesda, Md.

[73] Assignee: The United States of America as represented by the Secretary of the Army, Washington, D.C.

[21] Appl. No.: 446,174

[22] Filed: May 19, 1995

Related U.S. Application Data

[63] Continuation of Ser. No. 601,090, Oct. 22, 1990, abandoned, and a continuation-in-part of Ser. No. 202,509, Jun. 2, 1988, abandoned.

[51] Int. Cl.[6] ............................. A61K 39/02; A61K 45/05
[52] U.S. Cl. .................................... 424/278.1; 424/234.1; 424/258.1; 424/450; 536/117
[58] Field of Search .............................. 424/184.1, 193.1, 424/197.11, 278.1, 279.1, 282.1, 450, 234.1, 258.1; 530/300, 359, 868; 536/117

[56] References Cited

U.S. PATENT DOCUMENTS

| | | | |
|---|---|---|---|
| 4,029,762 | 6/1977 | Galanos et al. | 424/87 |
| 5,019,394 | 5/1991 | Hamaguchi | 424/423 |
| 5,026,557 | 6/1991 | Estis et al. | 424/450 |
| 5,059,421 | 10/1991 | Loughrey | 424/417 |
| 5,059,591 | 10/1991 | Janoff | 514/31 |

FOREIGN PATENT DOCUMENTS

| | | | |
|---|---|---|---|
| WO 84/04458 | 11/1984 | WIPO | A61K 39/00 |
| 0 217 527 | 4/1987 | WIPO | C12P 21/00 |

OTHER PUBLICATIONS

Alving, C.R., et al., Immunology Letters 25:275–280 (1990), Liposomes containing lipid A: a potent nontoxic adjuvant for a human malaria sporozoite vaccine.
Dijkstra, J., et al., J. Immunology 138:2663–2670 (April 15, 1987), "Modulation of the biological activity of bacterial endotoxin by incorporation into liposomes".
Fries, L. F., et al., P.N.A.S. (USA) 89:358–362 (1992), "Liposomal malaria vaccine in humans: A safe and potent adjuvant strategy".
Herbert, W. J. in *Handbook of Experimental Immunology*, edited by D. M. Weir (1973), Mineral–oil adjuvants and the immunization of laboratory animals. pp. A2.1–A2.14.

Richards, R. L., et al., Infection and Immunity 56:682–686 (Mar., 1988), Liposomes, lipid A, and aluminum hydroxide enhance the immune response top a synthetic malaria sporozoite antigen.
Richards, R. L., et al., Vaccine 7:506–512 (Dec. 1989), "Immunogenicity of liposomal malaria sporozoite antigen in monkeys: adjuvant effects of aluminum hydroxide and non–pyrogenic liposomal lipid A".
Schedel, I., Infection 16:4/8–7/11 (1988), "New aspects in the treatment of Gram–negative bacteraemia and septic shock".
Schuster, B. G., et al., J. Immunology 122:900–905 (1977), "Production of antibodies against phosphocholine, phosphatidylcholine, sphingomyelin, and lipid A by injection of liposomes containing lipid A".
Fitzer–Schiller, G., Washington Post, p. D3 (Jan. 19, 1993), "Cetocor stops trials of flagship drug".
Spalding, B. J., Bio/Technology 11:428–429 (11 Apr. 1993), "In shocking Synergen, sepsis tallies third victim".
Stone, R., Science 259:1243 (26 Feb. 1993), "Biotech industry reels on sepsis drug news".
Vosika, G. J., et al., Cancer Immunology and Immunotherapy 18:107–112 (1984), Phase–I study of intravenous modified lipid A.
Wenzel, R. P., The New England Journal of Medicine 326(17):1151–1152 (Apr. 23, 1992), "Anti–endotoxin monoclonal antibodies—a second look".
Braude, A., et al. *Infectious Dis. and Medical Microbiology* (1986) W.B. Saunders Co. Philadelphia pp. 51–60.
Takada, H., et al. CRC Crit. Rev. Microbiol. 16(6):476–523 (1989), "Structural requirements of lipid A for endotoxicity and other biological activities".
Chedid, L. in *Synthetic Vaccines*, R. Arnon (ed), 787 CRC Press, Boca Raton, Fl. pp. 94–103.
Ziegler, E.J. et al. N.E.S. Med. 307(20):1225–1230. Nov. 11, 1982. "Treatmnet of Gram–negative bacteremis".
P.N. Shek, et al; Immunology 47:627–632 (1982), "Immuneresponse mediated by liposome–associated protein antigens".

*Primary Examiner*—Thomas M. Cunningham
*Attorney, Agent, or Firm*—Charles H. Harris; John Francis Moran

[57] ABSTRACT

This invention is directed to the production of antibodies against lipid A by using encapsulating slow-releasing delivery materials or devices containing concentrations of lipid A that are greater than could be given safely to humans in the absence of said materials or devices. The antibodies to lipid A can be used for binding the antibodies to the lipid A that are present in the lipopolysaccharide that coats the surface of the Gram-negative bacteria.

29 Claims, 12 Drawing Sheets

ENCAPSULATED HIGH-CONCENTRATION LIPID A COMPOSITIONS AS IMMUNOGENIC AGENTS TO PRODUCE HUMAN ANTIBODIES TO PREVENT OR TREAT GRAM-NEGATIVE BACTERIAL INFECTIONS

RELATED APPLICATIONS

This application is a continuation of U.S. patent application Ser. No. 08/601,090, filed Oct. 22, 1990, now abandoned, which is a continuation-in-part of U.S. patent application Ser. No. 07/202,509, filed Jun. 2, 1998, now abandoned.

GOVERNMENT INTEREST

The invention described herein may be manufactured, licensed and used by or for governmental purposes without the payment of any royalties to us thereon.

TECHNICAL FIELD OF INVENTION

This invention relates to encapsulated high-concentration lipid A compositions and human monoclonal antibodies as immunotherapeutic agents to prevent or treat Gram-negative bacterial infections.

BACKGROUND OF THE INVENTION

Gram-negative Bacterial Infection

Throughout the world, sepsis caused by infection with Gram-negative bacteria is one of the major causes of death. Gram-negative bacteria are ubiquitous in the environment, and are present in the air, water, food, and are present in particularly high concentrations in the intestines. The surface of the skin is coated with Gram-negative bacteria and many skin infections are caused by these organisms. Because of their widespread distribution these bacteria cause opportunistic infections in association with other afflictions. For example, it is widely believed that sepsis is the most common cause of death in hospitals, and is particularly associated with conditions such as cancer, traumatic injury, and burns. A major cause of death in association with burns on the skin is infection and sepsis caused by gram-negative Pseudomonas organisms. Most urinary tract infections are caused by Gram-negative organisms. Individuals who are weakened by chronic diseases, or who have massive traumatic or burn injuries, or who have penetrating injuries of the intestines, are particularly at risk for developing life-threatening Gram-negative sepsis. Gram-negative infections that cause diarrhea are one of the major causes of death in infants.

The normal treatment of Gram-negative sepsis is by the administration of antibiotics that are active against sensitive organisms. The widespread use of such antibiotics has led to the continuous emergence of resistant strains of organisms and this has limited the effectiveness of antibiotic treatment. In addition, treatment often depends upon prompt administration of the appropriate antibiotic, but definitive laboratory tests to prove that the organism is sensitive to the antibiotic and that the optimally potent antibiotic is being used normally involves isolation and growth of the Gram-negative organism and inhibition by candidate antibiotics. Sensitivity tests normally require at least 1–2 days to perform, and because of urgency of many infections inadequate or suboptimal antibiotic therapy is often employed.
Immunotherapy with Lipid A Suboptimal antibiotic use is one of the major factors responsible for emergence of antibiotic-resistant organisms. A new strategy of immunotherapy has been developed for the treatment of Gram-negative sepsis. This technique involves the administration of monoclonal (or polyclonal) human antibodies having specificity against lipid A. The monoclonal or polyclonal antibodies to lipid A that are used for immunotherapy are given by intravenous administration in individuals who have sepsis, and are usually used only when a relatively large infection has already become established. These individuals are frequently already in a toxic condition that renders the treatment by immunotherapy more difficult.

Structure of Lipid A

The rational for the above immunotherapeutic approach is based on the fact that nearly all Gram-negative bacteria contain lipid A as a major element in the lipopolysaccharide molecules that coat the surface of all Gram-negative bacteria. The general structure of lipopolysaccharide is as follows:

(oligosaccharide repeating unit )$_n$-(core oligosaccharide)-(ketodeoxyoctonate)$_3$-lipid A The structure of lipid A has been completely defined for most Gram-negative bacteria, and it has been totally synthesized. It consists of a backbone of (B-1,6)-linked D-glucosamine disaccharide which carries phosphate residues in the positions 1 and 4'. Amidated or esterified long-chain fatty acids (generally D-3-hydroxy and/or acyloxy fatty acids) are present in each of the possible sites in the glucosamine moieties. Minor differences in structures of lipid A occur in molecules derived from various bacteria. In addition, so called "native" lipid A (i.e., unmodified lipid A derived by isolation from Gram-negative bacteria) usually consists of a mixture of molecules having the same basic structure as the "complete" lipid A described above but with differing degrees of phosphorylation or different numbers or structures of fatty acids. The monophosphoryl lipid A, that has reduced toxicity, lacks the phosphate residue at position 1.

Toxicity of Lipid A

A further useful approach to immunotherapy of Gram-negative bacteria would be in the development of a vaccine (i.e., immunoprophylaxis) against lipopolysaccharide via its lipid A component. A major theoretical and practical impediment to this approach is posed by the extremely high level of toxicity of lipopolysaccharide. A synonym for lipopolysaccharide is the term "endotoxin", and all of the endotoxic activity of lipopolysaccharide is caused by the lipid A component.

Lipopolysaccharide has literally dozens of biological activities when it is studied with in vitro biological systems or when it is injected in vivo. Many of these activities are associated with toxicity and are responsible for the adverse reactions that commonly observed in the course of Gram-negative bacterial infections and sepsis. Among these activities are included: pyrogenicity, neutropenia, thrombocytopenia, hypotension and shock, shock lung, renal failure, cachexia, and death. All of these toxic effects are caused by the lipid A component of lipopolysaccharide. Accordingly, there is a need for compositions which contain high concentrations of shielded or "hidden" lipid A which permits the slow release of lipid A therefrom thereby avoiding the deleterious and lethal results caused by the presence of high concentration of neat lipid A in the body.

SUMMARY OF THE INVENTION

It is therefore an object of the present invention to provide a novel immunoreactive composition comprising as an active ingredient a lipid A-containing component wherein the lipid A is sequestered, embedded or "hidden" in pharmaceutically-acceptable encapsulating-delivery material, said material being capable of (a) physically sequestering, "hiding" or shielding hydrophobic fatty acid portion of the lipid A from its aqueous environment, thereby preventing said portion from expressing its toxic properties in the host-mammal and (b) slowly releasing the lipid A from said material at a dose level within the range of 185 to 2,200 micrograms. The lipid A can be native lipid A, monophosphoryl lipid A or diphosphoryl lipid A. It has been found that high concentrations within the ranges of 185 to 219, 220 to 549, 550 to 1099, and 1100 to 2200 micrograms are especially useful in the practice of this invention. The encapsulating slow-releasing delivery materials or devices can be a liposome, biocompatible-biodegradable polymer, microcapsules, or microspheres, mechanical slow drug-releasing devices and combination thereof.

It is also an object of the present invention to provide a vaccine against Gram-negative bacterial infections and immunotherapeutic methods of treating a mammal prior to or following infection by Gram-negative bacteria including Escherichia, Salmonella, Pseudomonas, Proteus, Shigella, Vibrio, meningococcus and gonococcus.

Because of the toxicity of lipid A and the consequent difficulties in producing a satisfactory and effective human vaccine against this substance, it has been often proposed to utilize human polyclonal or monoclonal antibodies to lipid A as an immunotherapeutic product to treat individuals that are afflicted with Gram-negative bacterial infections [Ziegler, E. J. et al., Treatment of Gram-negative bacteremia and shock with human antiserum to a mutant *Escherichia coli*. New Eng. J. Med. 307:1225–1230 (1982); Teng, N. N. H. et al., Protection against Gram-negative bacteremia and endotoxemia with human monoclonal IgM antibodies. Proc. Natl. Acad. Sci. 82:1790–1794 (1984); Baumgartner, J. D. et al., Prevention of Gram-negative shock and death in surgical patients by antibody to endotoxin core glycolipid. Lancet ii:59–63 (13 Jul. 1985); Kirkland, T. N. et al, Analysis of the fine specificity and cross-reactivity of monoclonal anti-lipid A antibodies. J. Immunol. 137:3614–3619 (1986); Bogard, W. D. et al., Isolation and characterization of murine monoclonal antibodies specific for Gram-negative bacterial lipopolysaccharide: Association of cross-genus reactivity with lipid A specificity. Infect. Immun. 55:899–908 (1987); Ziegler, E. J. Protective antibody to endotoxin core: The emperor's new clothes? J. Infect. Dis. 158:286–290 (1988); Ward, D.C. et al., Monoclonal antibodies to salmonella lipopolysaccharide: functional analysis of anti-lipid A antibodies. Clin. Exp. Immunol. 72:157–163 (1988)]. Accordingly, it is a further object of this invention is to provide human antibodies in the form of "hyperimmune" polyclonal antiserum or a human monoclonal antibody reactive with Gram-negative bacteria and providing effective passive prophylaxis against or therapeutic treatment of sepsis caused by Gram-negative bacteria, said monoclonal antibody produced by a self-reproducing carrier cell containing genes that produce a protective human antibody.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

It has been discovered unexpectedly that an immunogenic composition containing a very high concentration of lipid A encapsulated within slow drug release materials such as liposomes, biocompatible-biodegradable polymers, microcapsules, microspheres, slow-release devices, or combinations thereof, can be injected systemically, including intramuscularly or subcutaneously, into a mammalian host. It has been established in the prior literature that the dose of lipid A, and specifically the dose of monophosphoryl lipid A (MPL), that can be administered safely to humans is limited by toxicity (Vosika, G. J. et al., Phase-I Study of intravenous modified Lipid-A. Cancer Immunol. Immunol. 18:107–112 (1984). The maximum safe intravenous dose of MPL was established as 100 ug of MPL per $m^2$. Assuming a normal surface area of 1.7 to 1.8 $m^2$, the maximum safe dose of MPL is 170 to 180 ug. Applicants have discovered that dose levels of the lipid A in the range of 185 to 2,200 micrograms can be administered to mammalian-hosts without toxic effect and result in the production of extremely high titers of antibodies, such that the antibody titers are higher than can be obtained with lower doses of lipid A.

The level of antibody activity to lipid A obtained was proportional to the dose of liposomal lipid A administered during the original single initial immunization. Even when the same total amount of liposomal lipid A was given in divided doses in multiple injections at different times the resultant antibody activity did not reach the levels achieved when the entire liposomal lipid A dose was given at a single time.

Suppression of Toxicity by using Encapsulating Materials

Experimental studies in animals have demonstrated that much of the toxicity of lipid A is accounted for by one of the phosphate groups (at position 1) and by the fatty acid moieties. Monophosphoryl lipid A has greatly reduced toxicity as determined by lessened pyrogenicity, but it has not lost all of the endotoxic character observed in native (diphosphoryl) lipid A. It is generally understood that lipid A that lacks fatty acid groups is nonpyrogenic, and the degree of pyrogenicity is related to the number of fatty acid groups that are present. Applicants, and others, have demonstrated in the literature that much of the toxicity of native lipid A, and much of the residual toxicity of monophosphoryl lipid A, can be suppressed by inclusion of lipid A into encapsulated materials, such liposomes [Ramsey, R. B. et al., Effects of lipid A and liposomes containing lipid A on platelet and fibrinogen production in rabbits. Blood A and liposome-associated lipid A with *Limulus Polyphemus* amoebocytes. Infect. Immun. 39:1385–1391 (1983); Dijkstra, J. et al., Modulation of the biological activity of bacterial endotoxin by incorporation into liposomes. J. Immunol. 138:2663—2670 (1987); Dijkstra, J. et al, Incorporation of LPS in liposomes diminishes its ability to induce tumoricidal activity and tumor necrosis factor secretion in murine macrophages. J. Leukocyte Biol. 43:436–444 (1988); Richards R. L., et al., Immunogenicity of liposomal malaria sporozoite antigen in monkeys; Adjuvant effects of aluminum hydroxide and non-pyrogenic liposomal lipid A. Vaccine 7:506–512 (1989); Alving, C. R. and Richards, R. L., Liposomes containing lipid A: A potent nontoxic adjuvant for a human malaria sporozoite vaccine. Immunol. Lett. 25:275–280 (1990)].

Liposomes consist of bilayers of lipids (such as phospholipids and other lipids) in which the hydrophobic regions of the lipids are oriented towards each other and the hydrophilic regions of the lipids are oriented toward the aqueous phase in which the lipids are suspended. The adjacent lipid molecules are held together by van der Waals forces and this results in the spontaneous formation of lipid sherules consisting of membranes containing lipid bilayers that surround internal aqueous spaces.

When lipid A in included in the lipid bilayer it can be demonstrated that anti-lipid A antibodies that are known to have specificities against the lipid headgroup (diglucosamine diphosphate) are readily bound to the liposomal lipid A. This can be shown to cause agglutination or complement fixation, and complement activation can cause lysis of the lipid bilayer resulting in increased permeability of the liposome to marker compounds present in the internal aqueous spaces. Other methods for performing the immunological studies could include using the liposomes containing lipid A as an antigen in enzyme-linked immunosorbent assays, or by using fluorescent antibodies or antibodies labeled with dyes, to "light up" and visualize the occurrence of the immunological reaction at the surface of the liposomes, or by using liposomes as absorbent particles to absorb antibodies. It is concluded from this that the lipid A molecule is oriented in the expected manner with the hydrophilic portion oriented toward the aqueous medium and the hydrophobic (fatty acid) portion buried in the lipid bilayer. Similar types of studies can be used to demonstrate that anti-lipid A antibodies can bind to lipid A that has been absorbed to erythrocytes.

An expected result of the orientation of lipid A that is described above might be that toxic effects caused by the fatty acid groups would be reduced or eliminated because of inaccessibility of the fatty acids to the aqueous environment. This result has indeed been observed. Our laboratory, and other laboratories, have demonstrated that neutropenia, interleukin-1 secretion, and pyrogenicity induced by lipid A in rabbits are all remarkably reduced when lipid A is present in liposomes [Ramsey, R. B. et al, Effects of lipid A and liposomes containing lipid A on platelet and fibrinogen production in rabbits. Blood 56:207–310 (1980); Dijkstra, J. et al., Modulation of the biological activity of bacterial endotoxin by incorporation into liposomes. J. Immunol. 138:2663–2670 (1987); Dijkstra, J. et al., Incorporation of LPS in liposomes diminishes ints ability to induce tumoricidal activity and tumor necrosis factor secretion in murine macrophages. J. Leukocyte Biol. 43:436–444 (1988); Richards R. L. et al., Immunogenicity of liposomal malaria sporozoite antigen in monkeys: Adjuvant effects of aluminum hydroxide and non-pyrogenic liposomal lipid A. Vaccine 7:506–512 (1989); Alving, C. R. and Richard, R. L., Liposomes containing lipid A: A potent nontoxic adjuvant for a human malaria sporozoite vaccine. Immunol. Lett. 25:275–280 (1990)]. One widely used measure of endotoxic activity is the use of the Limulus amebocyte lysis (LAL) test. In this test, the lysate from the amebocyte of Limulus polyphemus, is coagulated in the presence of endotoxin. This test is one of the most sensitive tests for the presence of endotoxin. We were able to reduce the LAL activity more than 10,000-fold by incorporating native lipid A in liposomes. However, we found that the LAL activity of liposomal lipid A was dependent on the epitope density of lipid A in the liposomes, and that by greatly increasing or decreasing liposomal lipid A concentration we could produce so-called "limulus-positive" or "Limulus-negative" liposomes, respectively [Ramsey, R. B. et al., Effects of lipid A and liposomes containing lipid A on platelet and fibrinogen production in rabbits. Blood 56:207–310 (1980); Richardson, E. C. et al., Interactions of lipid A and liposome-associated lipid A with Limulus polyphemus amoebocytes. Infect. Immun. 39:1385–1391 (1983); Dijkstra, J. et al., Modulation of the biological activity of bacterial endotoxin by incorporation into liposomes. J. Immunol. 138:2663–2670 (1987)]. Based on this it is clear that liposomes containing very high concentrations of lipid A can exhibit biological activities that are qualitatively different than liposomes containing lesser amounts of lipid A. Furthermore, liposomal lipid A per se can have properties that are qualitatively different than those of nonliposomal lipid A.

Lack of Toxicity of Liposomal Lipid A in Humans

Based on the perception that liposomes containing lipid A would be expected to have reduced toxicity in vivo, monophosphoryl lipid A was included in liposomes that were employed as a candidate vaccine for human malaria (*Plasmodium falciparum*). These liposomes also contained a recombinant antigen that was used for immunizing against the malaria. The liposomal lipid A served as an adjuvant for enhancing the immunogenicity of the recombinant antigen and the liposomes themselves were also absorbed with another adjuvant, aluminum hydroxide (alum). The candidate vaccine was injected three times, for example at 0, 8–12, and 16–20 weeks, into five groups of human volunteers (5 volunteers were in group 1, 6 in groups 2–4, and 7 in group 5). Increasing doses were sequentially injected in order to test the safety of the vaccine but each group received exactly the same dose of alum. Vaccine doses were as follows, based on dilution of the liposomes: group 1, 1:100; group 2, 1:10; group 3, 1:4;, group 4, 1:2; group 5, 1:1 (i.e., undiluted). Group 5 received 2.2 mg of monophosphoryl lipid A during each intramuscular injection, and to our knowledge this is the highest dose of lipid A that has ever been purposely given to a human subject. A previously published study with free monophosphoryl lipid A given intravenously to human volunteers demonstrated that the highest safe dose that could be used in humans was approximately one-twelfth of the maximum dose that we administered intramuscularly in liposomes. At the one-twelfth dose of intravenous free monophosphoryl lipid A a considerable level of reactogenicity and toxicity was observed (Vosika et al., Phase-I study of intravenous modified Lipid-A. Cancer Immunol. Immunol. 18:107–112 (1984). In contradistinction, applicants found that even at the highest does of monophosphoryl lipid A no significant acute toxic effects were observed.

Induction of Antibodies to Lipid A in Humans

Upon examining the sera of individual volunteers for the presence of IgG antibodies to lipid A we observed that most of the sera contained antibodies against lipid A. We conducted our immunological test by solid-phase enzyme-linked immunosorbent assay (ELISA) with purified lipid A as an antigen in microtiter plate wells. Other methods for studying the immune reaction could have included numerous other standard procedures for measuring reactivity of antibodies with purified antigen, including radioimmunoassay, flocculation of antigen or of liposomes or cells containing antigen, complement fixation, immunofluorescence assays or other assays utilizing dyes as markers, and hemagglutination of erythrocytes coated with lipid A, and hemagglutinin-inhibition assays with the same type of erythrocytes. All of the above assays, and others similar to them, are variations on the same theme of antigen-antibody reactions and are standard in the art. We made the quite unexpected discovery that although each group of volunteers contained individuals whose serum contained both IgG and IgM antibodies to lipid A, and that elevations were invariably based on comparison with preimmunization control samples drawn prior to injection of the vaccine, the IgG antibody titers increased substantially among the individuals injected with increasing doses of lipid A, and the highest levels of antibodies were observed in group 5. We concluded therefore that the optimal immune results of antibody levels against lipid A were achieved only with doses of lipid A that could not be safely given in the absence of liposomes. We concluded that this procedure is the only apparent safe method yet described for achieving maximum levels of IgG antibodies, and such levels of antibodies were achieved even at the first bleeding time (two weeks).

It should be pointed out that one of the striking observations that we made is that we produced antibodies against native lipid A by immunizing with liposomes containing monophosphoryl lipid A.

In the prior art it has been demonstrated that the phosphate residue in the C1 position of lipid A can contribute to the specificity to antibodies against lipid A. Indeed, polyclonal antisera to native lipid A have been described in which antibodies in the antisera did not react with analogues of lipid A that contained the position C4' phosphate but lacked the position C1 phosphate (Brade et al., Infection and Immunity, vol 55, pp 2636–2644, Nov. 1987; see the summary of FIG. 3 and Table 11 therein that summarizes the "type e" antibody specificity). Likewise, in the same publication it is taught conversely that antisera can be demonstrated that cannot react with lipid A analogues that include the C4' phosphate (antibody type d in the above Table 1). Based on this it is evident from the prior art that it is not established that antibodies to monophosphoryl lipid A (i.e., lipid A that lacks the position 1 phosphate) will necessarily react with native lipid A. In at least some instances position 1 phosphate is a critical immunodominant factor that mainly determines the specificity of the antibodies against native lipid A. In of the complex specificities that are generated by immunizing with lipid A it is not obvious that immunizing with a derivative of lipid A lacking a phosphate group (e.g., monophosphoryl lipid A) would induce antibodies against the native lipid A containing the phosphate group. Brade et al. have demonstrated that antibodies to lipid A can be produced (type e antibodies) that require the presence of the C1 phosphate group that is lacking in monophosphoryl lipid A. It is not obvious that such anti-C1-phosphate antibodies would not be uniquely induced by liposomal native lipid A. Accordingly, if anti-C1-phosphate antibodies were exclusively induced by Liposomal Lipid A they could not have been induced by immunizing with liposomal monophosphoryl lipid A that lacks the C1-phosphate group.

Proposed Strategies for use of Liposomal Anti-Sepsis Vaccine

We anticipate that a liposomal anti-sepsis vaccine could be used either for immunoprophylaxis (as with other types of vaccines in their conventional usage forms) or as an immunotherapeutic agent in individuals who have already developed sepsis or individuals at risk for developing sepsis (e.g., patients subjected to traumatic injuries or to burns, or patients who are debilitated because of old age or chronic diseases such as cancer or diseases that might cause a prolonged bedridden state). The results indicate that the vaccine would be effective within two weeks after administration, but the extremely high levels achieved in group 5 suggest that the vaccine could be effective even at earlier times. The vaccine could be used in conjunction with other therapeutic measures, such as correction of the underlying inciting condition (e.g., removal of abscess, removal of cancer, closing of perforated intestines, removal of infected intravenous catheters, replacement of infected heart valves, etc.), or with concurrent administration of antibiotics, steroids, anticancer drugs, or immunotherapeutic or any other therapeutic measures that would normally be expected to have therapeutic benefit in the absence of the liposomal anti-sepsis vaccine.

Another unexpected benefit from our anti-sepsis vaccine appeared to be that the high titers of antibody activity that were achieved at the highest initial dose of vaccine (group 5) could not be duplicated simply by giving multiple immunizations with a smaller dose of vaccine. The IgG anti-lipid A levels of group 5 observed after two weeks were higher than the highest levels ever observed in any of the other groups, even after subsequent immunizations that resulted in doses of lipid A that were equivalent to those that were given initially in group 5. In the FIG. 1, each group received a boosting immunization at either 8 weeks (groups 1–3) or 10 weeks (groups 4 and 5) that was identical to the original immunization dose. Therefore, after the second (boosting) immunization group 4 received a total dose of liposomal monophosphoryl lipid A in two injections that was identical to the dose of lipid A that was present in the single initial immunization dose of group 5. Despite this, when measured 2 weeks after the boosting immunization, group 4 achieved an IgG antibody level that was only slightly more than half as high as the level achieved 2 weeks after the initial immunization with the twice the antigen dose given to the volunteers in group 5.

Expectation of Similar Results with Other Strategies

The net result of the use of liposomes containing lipid A is that the fatty acids of lipid A are "hidden" from the aqueous environment. This result presumably could also be accomplished by other types of particles or strategies. For example, polymers of various types, microcapsules, and microspheres all would be expected to accomplish the same result. Although the terms "liposomes", "microcapsules", "microspheres", "polymeric drug delivery vehicles", "slow release devices", or other similar terms are often used informally in the literature to describe various types of carrier systems for drugs and proteins, there is no universal agreement, nor are there any generally accepted national or international conventions, that define the meanings of such nomenclature. Liposomes are ordinarily understood to consist of lipid membranes that are capable of enclosing an internal aqueous space and the membranes may consist of a variety of types of lipids. Methods for manufacturing liposomes are described in U.S. patent application Ser. No. 07/202,509 filed 2 Jun. 1988, of which the present specification is a continuation-in-part. There is no necessary requirement for the presence of a closed membrane, only a requirement that the lipids self-associate such that they form a particulate structure. Among the lipids that have been used either alone or in combination with other lipids to construct liposomes are included phospholipids, glycolipids, glycophospholipids, diglycerides, triglycerides, sterols, steroids, terpenoids, free fatty acids, and lipoidal vitamins. Numerous liposomal constructs have been made that contain synthetic fatty acyl groups conjugated to proteins or other polymers. Liposomes may also be formed that use lipids to reconstitute insoluble hydrophobic proteins. The terms "microcapsule" or "microsphere" in the present specification refer to particulate constructs that are used as carriers for antigenic molecules (such as lipid A), and the molecules that form the constructs, whether they are liposomes, lipids, proteins, or various other types of polymers, provide a diffusion barrier to prevent immediate release of the antigenic material. Slow release of the antigenic material to the immune system is promoted by these constructs.

Release of encapsulated materials from particles such as those comprised of polymers most commonly occurs by diffusion. The diffusion mechanisms of materials from polymers are multitudinous, including: release from a reservoir surrounded by a polymeric film; release from a matrix in which the material to be released is distributed uniformly through the polymer; cleavage of the material from a polymer backbone; dissolution of the polymer by exposure to an environmental solvent; permeation by water leading to leakage due to osmotic swelling either by creating pores in the polymer or through preformed pores; and release of material by imposition of external magnetic fields. The net result of each of these mechanisms is initial sequestration and "hiding" of the material to be released, followed by a relative degree of slow release that is regulated by the release mechanism and by the nature of the polymeric microcapsule or microsphere chemical and physical composition. These mechanisms are described in further detail by in Langer, R., New methods of drug delivery. Science 249:1527–1533 (1990). Langer also points out that the diffusion and release mechanisms outlined above can apply to immunological applications including antibody production against encapsulated or sequestered antigen. We also have evidence that liposomes containing lipid A serve as "slow release" devices. We found that a considerable fraction (perhaps as much as half) of a formulation of fluorescence-labeled liposomes containing lipid A that we injected intramuscularly in mice remained at the injection side for at least a week. Slow release of the toxic lipid A might cause a nontoxic but highly immunogenic stimulus. The slow release of lipid A could be accomplished by any type of particle or device that is designed to release drugs or other therapeutic substance in vivo.

DETAILED DESCRIPTION OF THE INVENTION EXAMPLES

Figure 1:
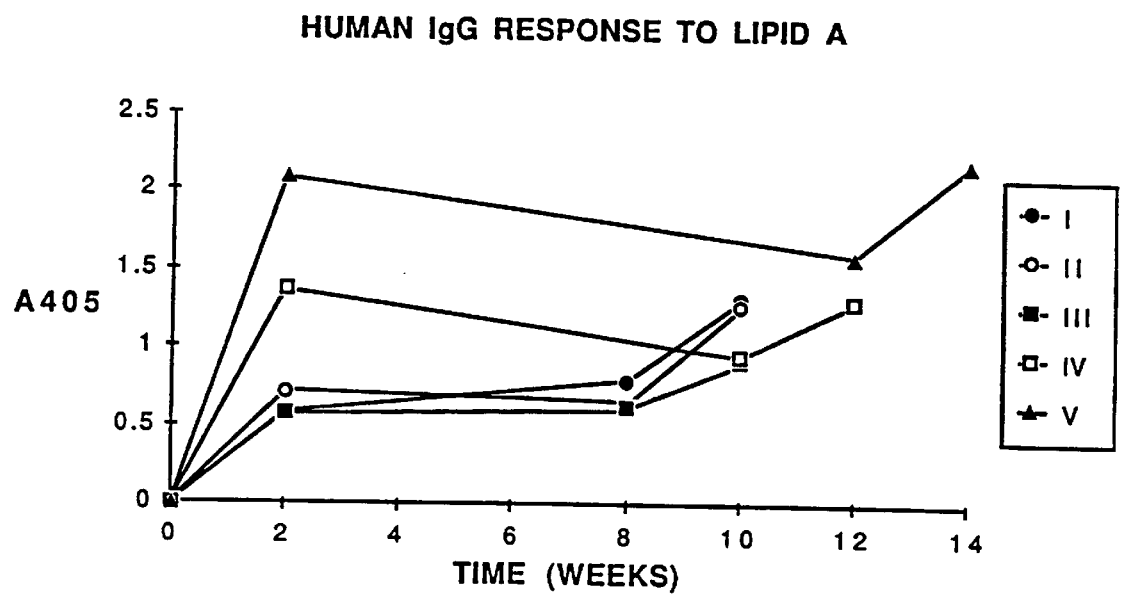
FIG. 1 shows human IgG Responses to lipid A. The IgG antibody levels to native lipid A were measured by ELISA and are shown as absorbance at 405 nm of a 1/100 dilution of the serum. Each line represents the mean of the values observed in the individual human sera in each group. Each group was immunized with liposomes containing DMPC, DMPG, CHOL, lipid A and R32NS1. Prior to injection the liposomes were diluted, as indicated below, and mixed with alum as adjuvant. Group V was immunized with liposomes containing 2.2 mg of monophosphoryl lipid A. This vaccine was diluted 1/2, 1/4, 1/10, and 1/100, respectively for groups IV, III, II, and I prior to immunization. Groups I, II, and III were immunized at 0 and 8 weeks; group IV was immunized at 0 and 10 weeks; and group V was immunized at 0 and 12 weeks. The data demonstrate that a single injection with undiluted vaccine (group V at 0 weeks) resulted in a higher immune response 2 weeks later (and even 12 weeks later) than two injections of a 1/2 dilution (group IV).
Figure 2:
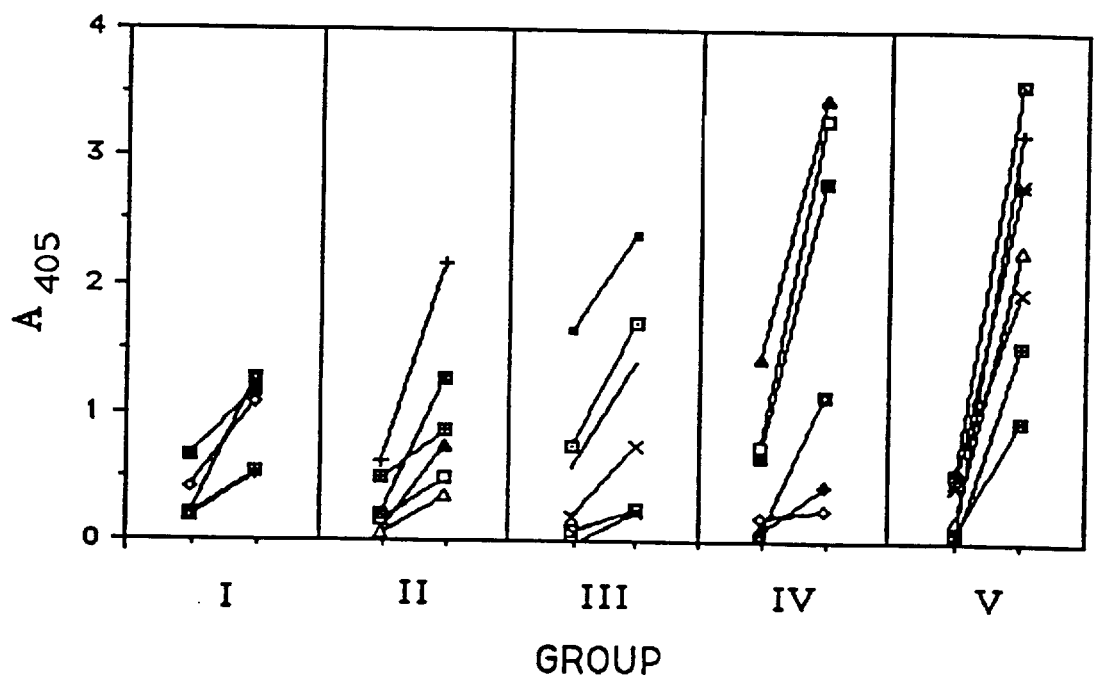
FIG. 2 shows Individual IgG Responses to Lipid A. This shows the responses at 0 and 2 weeks after injection in each of the 5 groups. This shows that all of the volunteers in group v developed substantially higher levels of antibodies to lipid A after immunization. The data also show that certain individuals have high levels of antibodies to lipid A even prior to immunization.
Figure 3:
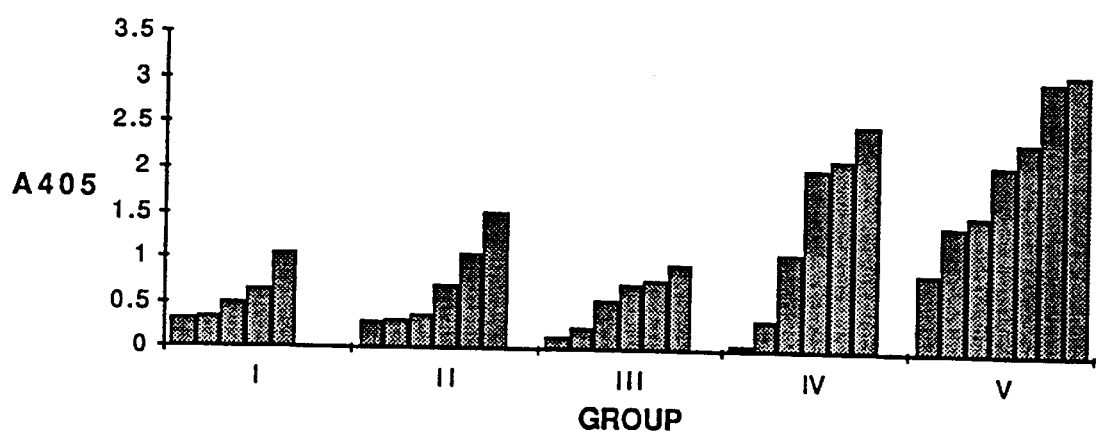
FIG. 3 shows Individual IgG Responses to Lipid A. This shows that when the preimmunization levels of antibodies to lipid A are subtracted in each volunteer serum, the group V individuals had the most consistent and the highest levels of antibodies to lipid A induced by immunization.
Figure 4:
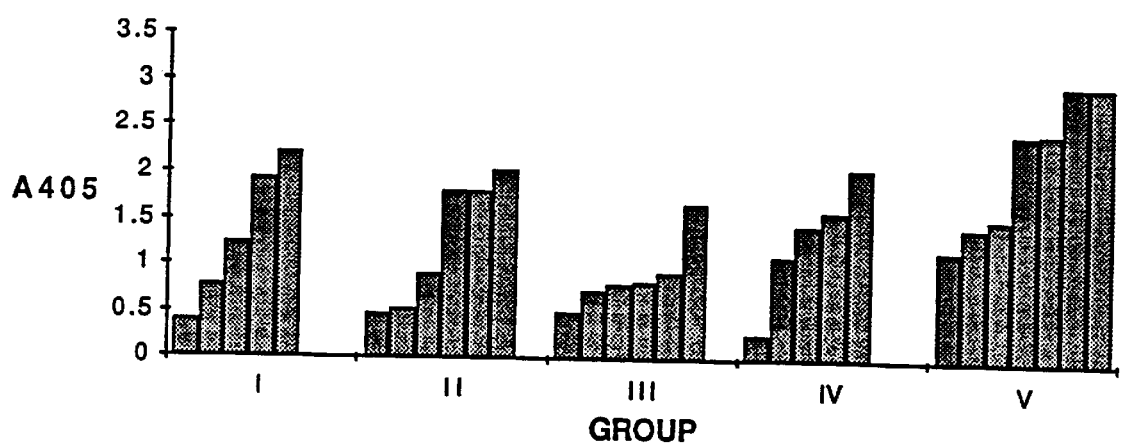
FIG. 4 shows Individual Human IgG Responses to Lipid A Two Weeks Following a Boosting Immunization. The boosting injection times are described in the legend to FIG. 1. Even after boosting immunization, group V outperformed all of the other groups in developing high individual antibody titers.
Figure 5:
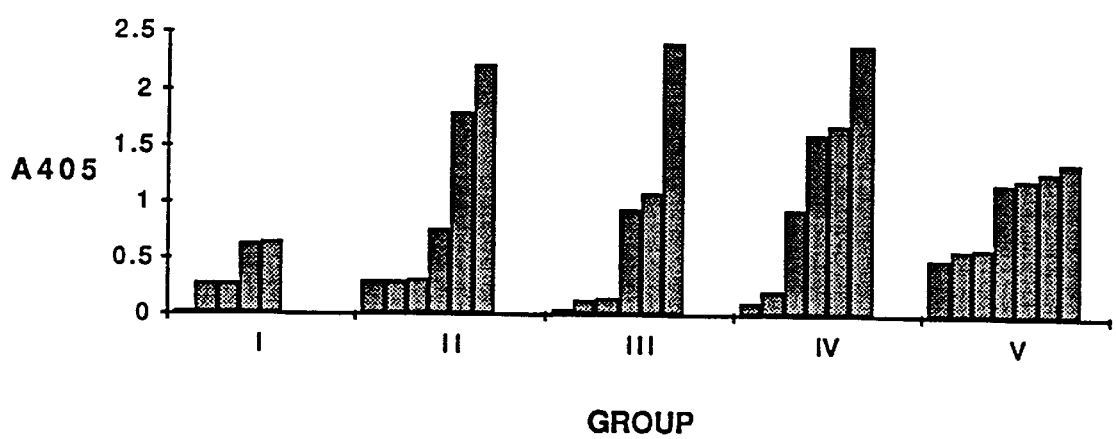
FIG. 5 shows Individual IgM Response to Lipid A. This shows that when the preimmunization levels of antibodies to lipid A are subtracted in each volunteer serum, the individuals in groups II, III, IV, and V had more consistent and the higher levels of antibodies to lipid A induced by immunization compared to group I. The most consistently elevated levels, showing that all individuals developed high levels, of IgM antibodies were observed in group V.
Figure 6:
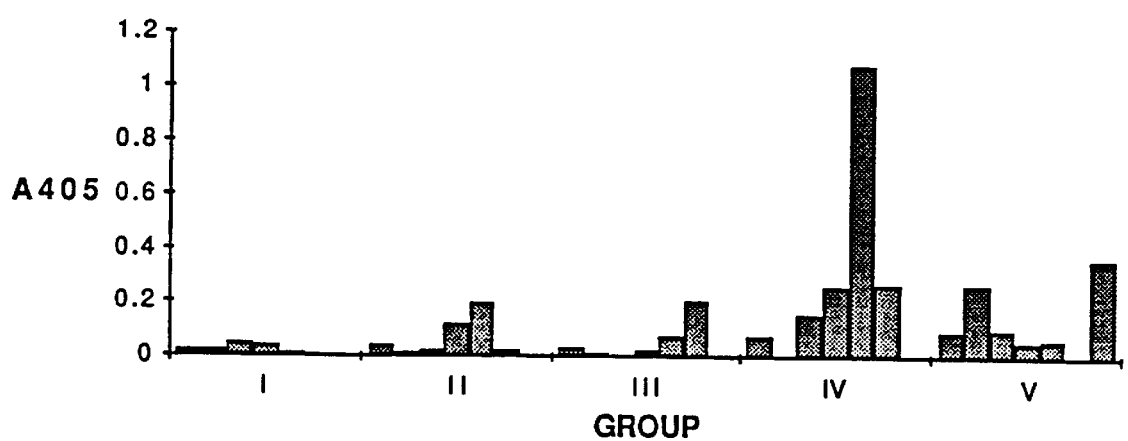
FIG. 6 shows Individual IgA Responses to Lipid A. This shows that individuals in groups II, III, IV, and V developed IgA antibodies to lipid A. The levels, particularly in groups IV and V, were more consistent and higher than in group I.
Figure 7:
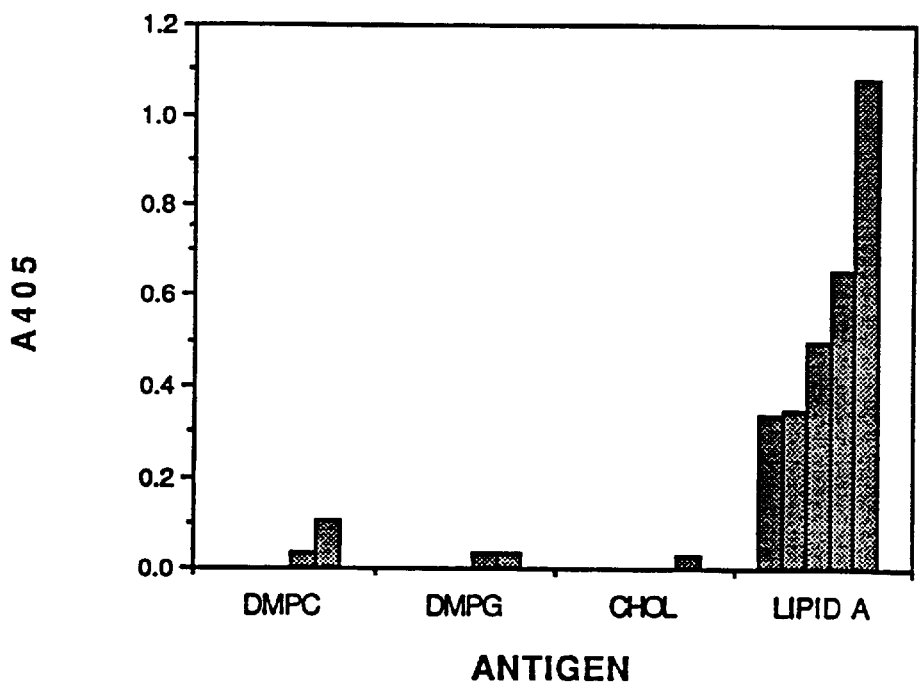
FIG. 7 shows IgG Response in Group I to Individual Liposome Constituents After Injection of Liposomes. The liposomes used for injection consisted of dimyristoyl phosphatidylcholine (DMPC), dimyristoyl phosphatidylglycerol (DMPG), cholesterol (CHOL), and monophosphoryl lipid A. Each of the components was individually tested by ELISA for the appearance of IgG antibodies against the purified individual component. In the case of lipid A, the individuals were injected with liposomes containing 0.022 mg of monophosphoryl lipid A, but the ELISA analysis was performed with purified native lipid A. The data are shown with preimmunization values, if any, subtracted from the postimmunization values (2 weeks after initial immunization). Each serum was diluted 1/100 for ELISA analysis. The predominant antibody activity in each case was developed against lipid A.
Figure 8:
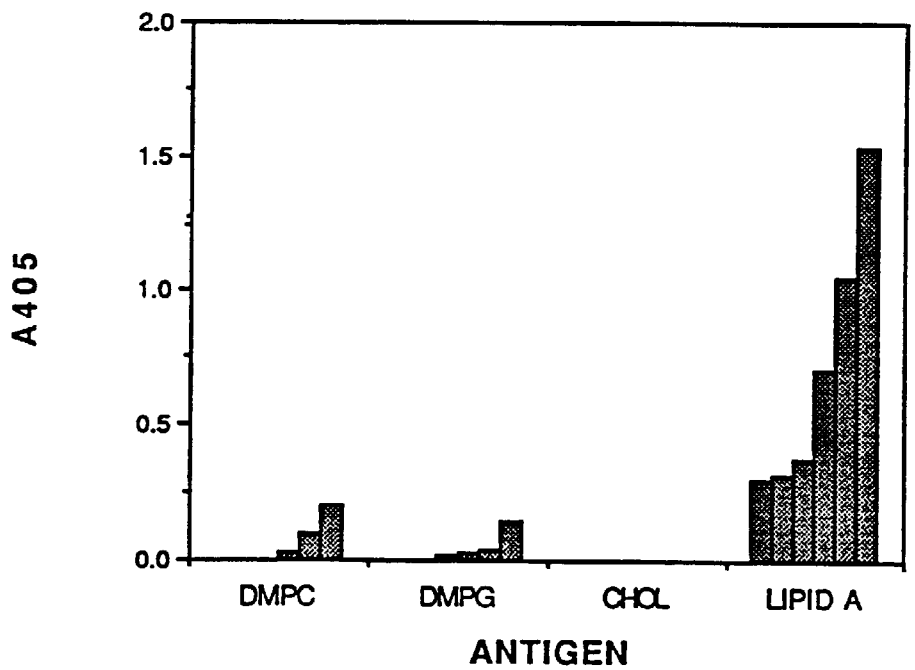
FIG. 8 shows IgG Responses in Group II to Individual Liposome Constituents After Injection of Liposomes. The liposomes used for injection consisted of dimyristoyl phosphatidylcholine (DMPC), dimyristoyl phosphatidylglycerol (DMPG), cholesterol (CHOL), and monophosphoryl lipid A. Each of the components was individually tested by ELISA for the appearance of IgG antibodies against the purified individual component. In the case of lipid A, the individuals were injected with liposomes containing 0.22 mg of monophosphoryl lipid A, but the ELISA analysis was performed with purified native lipid A. The data are shown with preimmunization values, if any, subtracted from the postimmunization values (2 weeks after initial immunization). Each serum was diluted 1/100 for ELISA analysis. The predominant antibody activity in each case was developed against lipid A.
Figure 9:
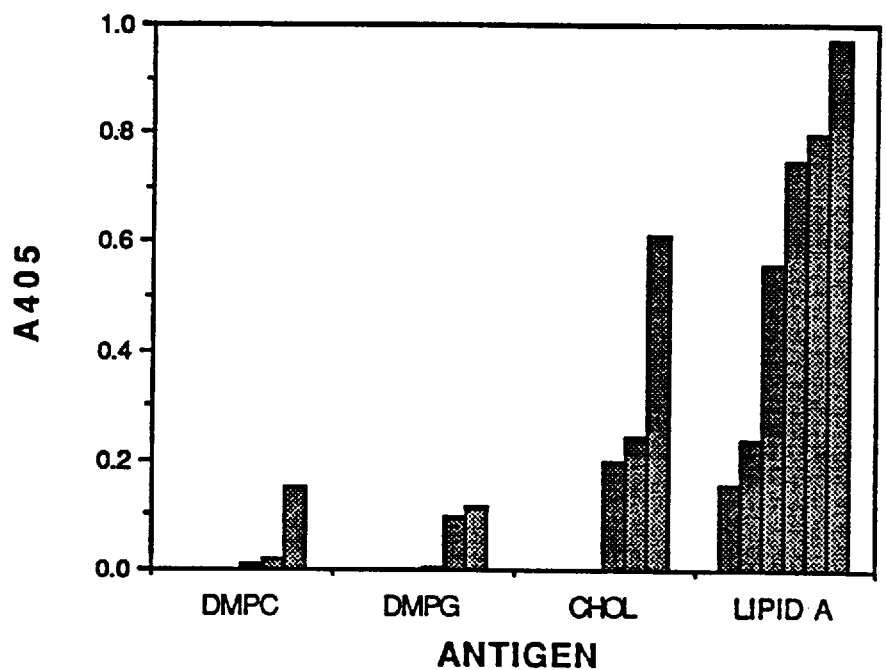
FIG. 9 shows IgG Responses in Group III to Individual Liposome Constituents After Injection of Liposomes. The liposomes used for injection consisted of dimyristoyl phosphatidylcholine (DMPC), dimyristoyl phosphatidylglycerol (DMPG), cholesterol (CHOL), and monophosphoryl lipid A. Each of the components was individually tested by ELISA for the appearance of IgG antibodies against the purified individual component. In the case of lipid A, the individuals were injected with liposomes containing 0.55 mg of monophosphoryl lipid A, but the ELISA analysis was performed with purified native lipid A. The data are shown with preimmunization values, if any, subtracted from the postimmunization values (2 weeks after initial immunization). Each serum was diluted 1/100 for ELISA analysis. The predominant antibody activity in each case was developed against lipid A.
Figure 10:
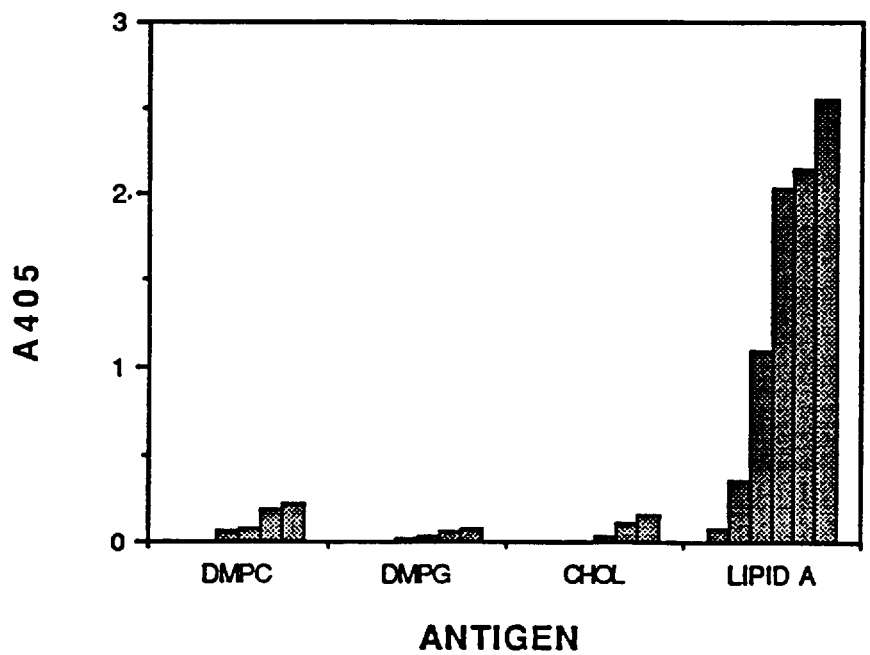
FIG. 10 IgG Responses in Group IV to Individual Liposome Constituents After Injection of Liposomes. The liposomes used for injection consisted of dimyristoyl phospatidylcholine (DMPC), dimyristoyl phosphatidylglycerol (DMPG), cholesterol (CHOL), and monophosphoryl lipid A. Each of the components was individually tested by ELISA for the appearance of IgG antibodies against the purified individual component. In the case of lipid A, the individuals were injected with liposomes containing 1.1 mg of monophosphoryl lipid A, but the ELISA analysis was performed with purified native lipid A. The data are shown with preimmunization values, if any, subtracted from the postimmunization values (2 weeks after initial immunization). Each serum was diluted 1/100 for ELISA analysis. The predominant antibody activity in each case was developed against lipid A.
Figure 11:
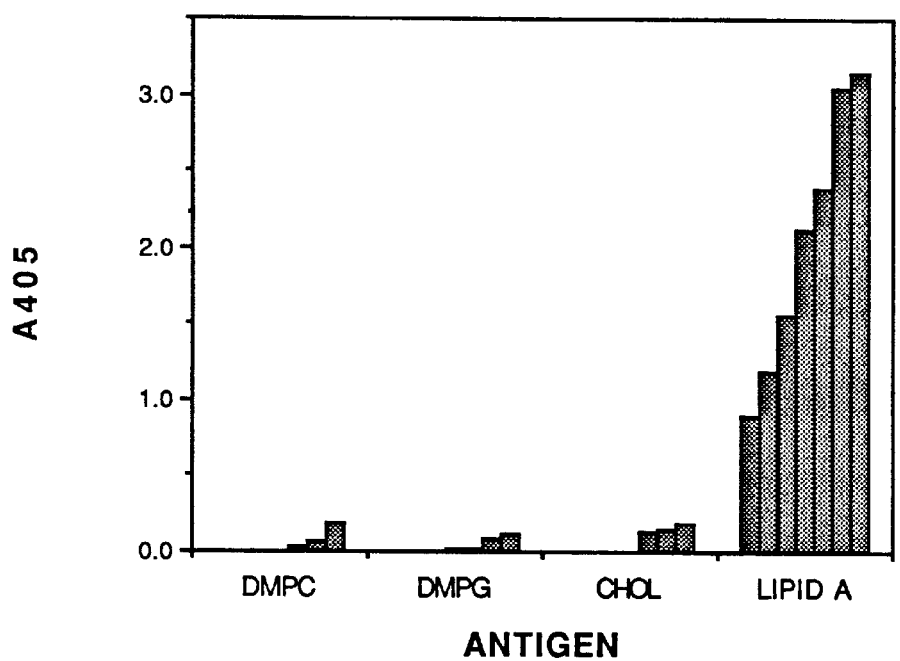
FIG. 11 IgG Responses in Group V to Individual Liposome Constituents After Injection of Liposomes. The liposomes used for injection consisted of dimyristoyl phosphatidylcholine (DMPC), dimyristoyl phosphatidylglycerol (DMPG), cholesterol (CHOL), and monophosphoryl lipid A. Each of the components was individually tested by ELISA for the appearance of IgG antibodies against the purified individual components. In the case of lipid A, the individuals were injected with liposomes containing 2.2 mg of monophosphoryl lipid A, but the ELISA analysis was performed with purified native lipid A. The data are shown with preimmunization values, if any, subtracted from the postimmunization values (2 weeks after initial immunization). Each serum was diluted 1/100 for ELISA analysis. The predominant antibody activity in each case was developed against lipid A.
Figure 12:
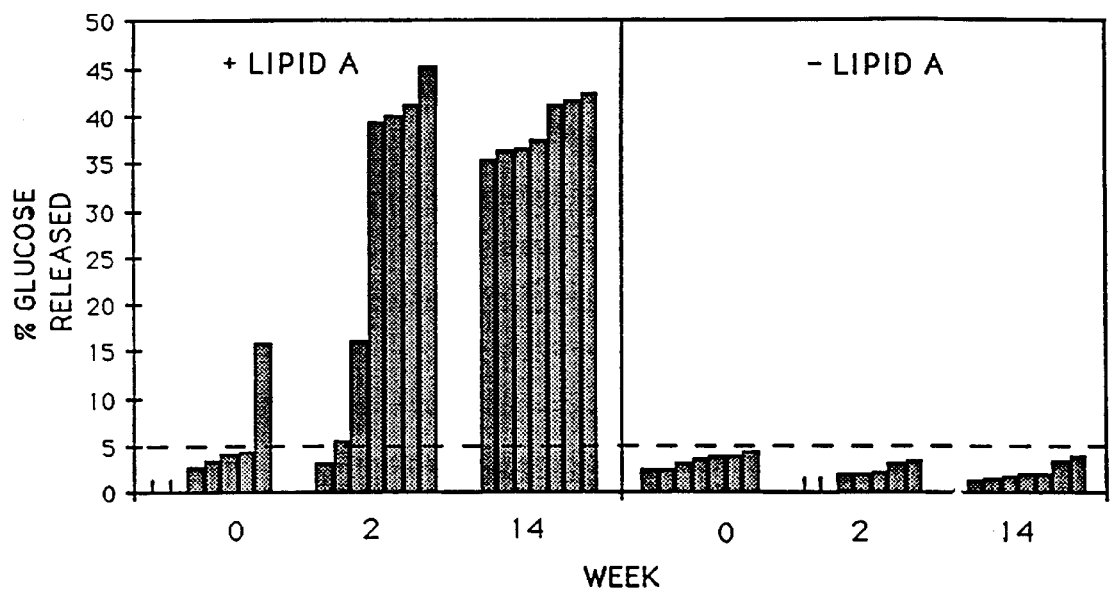
FIG. 12 Complement-Mediated Immune Damage to Membranes Induced by Antisera From Individuals in Group V. Complement-dependent lysis of liposomes leading to release of trapped glucose marker from inside the liposomes was measured with sera from each individual in group V taken at 0, 2 weeks and 14 weeks following immunization with liposomes containing DMPC, CHOL, DMPG, and monophosphoryl lipid A (2.2 mg). The complement-mediated lysis of liposomes containing or lacking native lipid A as an antigen was examined. The dashed line indicates an arbitrary value of glucose release that we have utilized in the past to indicate the level at which a significant amount of immune damage has occurred to the liposomes compared to the background variability in the assay. The results show that substantial immune damage occurred to the liposomes containing lipid A and that this was even increased at week 14. The ability to activate complement to cause membrane damage is a measure of the ability of the antiserum to activate a defense mechanism in the body to protect against infection with Gram-negative bacterial organisms.

The herein offered examples provide methods for illustrating, without any implied limitation, the practice of this invention in the production of immunoreactive compositions containing extremely high dose levels of lipid A that can be used to produce vaccines and human mono- and polyclonal antibodies reactive with lipid A.

The profile of the representative experiments have been chosen to illustrate methods of making immunotherapeutic compositions that result in the production of antibodies to lipid A that would be expected to be useful in the prevention and treatment of infections (sepsis) caused by Gram-negative bacteria.

Experimental Methods and Result

Preparation of Liposomes. Liposomes for immunization were prepared from a mixture of dimyristoyl phosphatidylcholine (DMPC), dimyristoyl phosphatidylglycerol (DMPG), and cholesterol (Chol) in molar ratios of 1.8/0.2/1.5. DMPC and DMPG were purchased from Avanti Polar Lipids, Pelham, Al.. Chol was purchased from Sigma Chemical Co., St. Louis, Mo. and was recrystallized three times from ethanol before use. Monophosphoryl lipid A (Ribi Immunochem Research Inc.) was incorporated in the liposomes at a concentration of 52.6 ug per umole of phospholipid. All lipids were prepared as solutions in redistilled chloroform. Following the additions of the appropriate volumes of lipid solutions into round bottom flasks, they were rotary evaporated until all the solvent was evaporated and a thin film of lipid was left on the flask wall. The flask was further dried in a desiccator under high vacuum overnight. The lipids were then hydrated with sterile pyrogen free water (USP) so that a phospholipid concentration of approximately 40 mM was achieved. The hydrated lipids were then aliquotted into vaccine bottles and freeze dried. After lyophilization, the bottles were stoppered under vacuum and stored at 4 degrees C. in the dark. At a later time the drug substance, SK & F 105154 (R32NS1), was injected into each bottle. The phospholipid concentration in the bottle was 250 mM after the reconstitution with the R32NS1. After an eighteen hour incubation, the bottles were hand shaken until all the lipid was suspended. The bottles were then washed with sterile PBS, pH 6.4 and centrifuged. After two more washes the liposomes were resuspended with PBS, pH 6.4. The liposomes were then dispensed, using aseptic technique, into vaccine bottles at 0.9 ml per bottle. Alum concentrate (Rehsorptar, Lot #C17502, Armour Pharmaceuticals, Kankakee, Ill.), diluted to the 1.2–1.8 mg Al/ml range with PBS, pH 6.4, was dispensed into each vaccine vial at a volume of 0.7 ml. The phospholipid concentration of the final product was 55 mM. The lipid A concentration was 2.9 mg/ml.

ELISAS. Enzyme-linked immunosorbent assays were performed utilizing lipid A from *S. Minnesota* R595 (List Biologics, Campbell, Calif.) as antigen. Wells of "U" bottom polystyrene microtitre plates (Immulon II, Dynatech Laboratories, Inc., Alexandria, Va.) were coated with 50 ul of an 0.02 ug/ul ethanolic solution of lipid A. Wells were allowed to air dry in a fume hood for approximately 1 hour. Plates not used immediately were stored at −20 degrees C. until use. Blocking buffer (PBS with 10% heat-inactivated fetal calf serum) was added to all wells at a volume of 100 ul and held at room temperature for 2 hours. Blocking buffer was removed by inversion of the plates followed by a sharp tap of the plate to remove all the well contents. Human sera were diluted 1:100 in blocking buffer and added to wells in triplicate at a volume of 50 ul per well. Following an eighteen hour incubation overnight at 4 degrees C, the contents of the wells were aspirated, the plates were washed three times with PBS alone, and 50 ul of the appropriate alkaline phosphatase-conjugated goat anti-human Ig (Kirkegaard & Perry Laboratories, Inc., Gaithersburg, Md.) was added to the wells. The conjugate was diluted in blocking buffer and added to the wells to give a final concentration of 5 ng per well. After an incubation of 2 hours at room temperature, the contents of the wells were aspirated, and the plates were washed three times with PBS alone. Then 50 ul of the substrate, p-nitro phenylphosphate, prepared in diethanolamine buffer was added to the wells and incubated 1 h at room temperature in the dark. The absorbance was read at 405 nm using a UV max kinetic plate reader (Molecular Devices, Palo Alto, Calif.) Values were reported after subtracting out values in wells which lacked only antigen.

We claim:

1. A method of inducing high levels of antibodies against native lipid A in a human without inducing significant toxicity, comprising:
administering a composition comprising lipid A and a pharmacologically acceptable excipient, wherein the hydrophobic fatty acid portion of the lipid A is sequestered within a pharmaceutically acceptable antigen delivery vehicle, and wherein the composition is non-toxic in humans,
such that the human receives a dosage of lipid A that has the immunological effect of a dose of greater than 100 $\mu g/m^2$ of monophosphoryl lipid A.

2. The method of claim 1, wherein the pharmaceutically acceptable antigen delivery vehicle is a liposome.

3. The method of claim 1, wherein the pharmaceutically acceptable antigen delivery vehicle is a biocompatible polymer.

4. The method of claim 1, wherein the pharmaceutically acceptable antigen delivery vehicle is a slow release device.

5. The method of claim 1, wherein the excipient is alum.

6. The method of claim 1, wherein the composition is administered prior to the onset of sepsis caused by a Gram-negative bacteria.

7. The method of claim 1, wherein the lipid A is selected from the group consisting of one or more of lipopolysaccharide, native lipid A, monophosphoryl lipid A, diphosphoryl lipid A, and immunogenic derivatives, subunit structures or degradation products thereof.

8. The method of claim 7, wherein the lipid A is monophosphoryl lipid A.

9. The method of claim 1, wherein the dosage of lipid A has the immunological effect of a dose of from greater than 100 $\mu g/m^2$ to about 1295 $\mu g/m^2$ of monophosphoryl lipid A.

10. A method of reducing the severity of sepsis in a human caused by a Gram-negative bacteria by inducing high levels of antibodies against native lipid A without inducing significant toxicity, comprising:
administering a composition comprising lipid A and a pharmacologically acceptable excipient, wherein the hydrophobic fatty acid portion of the lipid A is sequestered within a pharmaceutically acceptable antigen delivery vehicle, and wherein the composition is non-toxic in humans,
such that the human receives a dosage of lipid A that has the immunological effect of a dose of greater than 100 $\mu g/m^2$ of monophosphoryl lipid A.

11. The method of claim 10, wherein the Gram-negative bacteria is selected from the group consisting of Escherichia, Salmonella, Pseudomonas, Proteus, Shigella, Vibrio, Meningococcus and Gonococcus.

12. The method of claim 10, wherein the composition is administered to the human such that the composition induces a human monoclonal antibody reactive with an antigenic form of the lipid A, wherein the antibody is produced by a self-reproducing carrier cell containing genes that produce a protective human antibody.

13. The method of claim 10, wherein the composition is administered to the human such that the composition induces a human monoclonal antibody reactive with Gram-negative bacteria, wherein the antibody is produced by a self-reproducing carrier cell containing genes that produce a protective human antibody.

14. The method of claim 10, wherein the pharmaceutically acceptable antigen delivery vehicle is a liposome.

15. The method of claim 10, wherein the pharmaceutically acceptable antigen delivery vehicle is a biocompatible polymer.

16. The method of claim 10, wherein the pharmaceutically acceptable antigen delivery vehicle is a slow release device.

17. The method of claim 10, wherein the excipient is alum.

18. The method of claim 10, wherein the lipid A is selected from the group consisting of one or more of lipopolysaccharide, native lipid A, monophosphoryl lipid A, diphosphoryl lipid A, and immunogenic derivatives, subunit structures or degradation products thereof.

19. The method of claim 18, wherein the lipid A is monophosphoryl lipid A.

20. The method of claim 10, wherein the dosage of lipid A has the immunological effect of a dose of from greater than 100 $\mu g/m^2$ to about 1295 $\mu g/m^2$ of monophosphoryl lipid A.

21. A vaccine administrable to a human subject comprising
(i) lipid A, and
(ii) a pharmaceutically acceptable excipient;
wherein the hydrophobic fatty acid portion of the lipid A is sequestered within a pharmaceutically acceptable antigen delivery vehicle, the dosage of lipid A in said vaccine has the immunological effect of a dose of greater than 100 $\mu g/m^2$ of monophosphoryl lipid A, and the vaccine is non-toxic in humans.

22. The vaccine of claim 21, wherein the lipid A is selected from the group consisting of one or more of lipopolysaccharide, native lipid A, monophosphoryl lipid A, diphosphoryl lipid A, and immunogenic derivatives, subunit structures or degradation products thereof.

23. The vaccine of claim 22, wherein the lipid A is monophosphoryl lipid A.

24. The vaccine of claim 21, wherein the dosage of lipid A in said vaccine has the immunological effect of a dose of from greater than 100 $\mu g/m^2$ to about 1295 $\mu g/m^2$ of monophosphoryl lipid A.

25. The vaccine of claim 24, wherein the dosage of lipid A in said vaccine has the immunological effect of a dose of monophosphoryl lipid A selected from the dosage ranges consisting of 100 to 130 $\mu g/m^2$, 131 to 325 $\mu g/m^2$, 326 to 645 $\mu g/m^2$ and 645 to 1295 $\mu g/m^2$.

26. The vaccine of claim 21, wherein the antigen delivery vehicle is a slow release device.

27. The vaccine of claim 21, wherein the antigen delivery vehicle is a liposome.

28. The vaccine of claim 21, wherein the pharmaceutically acceptable antigen delivery vehicle is a biocompatible polymer.

29. The vaccine of claim 21, wherein the excipient is alum.

* * * * *